United States Patent
Meron et al.

(10) Patent No.: US 7,764,304 B2
(45) Date of Patent: *Jul. 27, 2010

(54) METHOD FOR ACTIVATING AN IMAGE COLLECTING PROCESS

(75) Inventors: Gavriel Meron, Kfar-Ganim (IL); Arkady Glukhovsky, Nesher (IL); Jerome Avron, Haifa (IL); Doron Adler, Nesher (IL)

(73) Assignee: Given Imaging Ltd., Yoqneam (IL)

( * ) Notice: Subject to any disclaimer, the term of this patent is extended or adjusted under 35 U.S.C. 154(b) by 483 days.

This patent is subject to a terminal disclaimer.

(21) Appl. No.: 11/905,677

(22) Filed: Oct. 3, 2007

(65) Prior Publication Data
US 2008/0033243 A1 Feb. 7, 2008

Related U.S. Application Data

(63) Continuation of application No. 10/130,326, filed as application No. PCT/IL00/00752 on Nov. 15, 2000, now Pat. No. 7,295,226.

(30) Foreign Application Priority Data
Nov. 15, 1999 (IL) .................................... 132944

(51) Int. Cl.
H04N 7/18 (2006.01)
A61B 1/04 (2006.01)
A61B 1/06 (2006.01)
(52) U.S. Cl. ................... 348/77; 600/109; 600/114
(58) Field of Classification Search ............ 348/76–77; 600/109, 114
See application file for complete search history.

(56) References Cited

U.S. PATENT DOCUMENTS 5,365,267 A 11/1994 Edwards

FOREIGN PATENT DOCUMENTS

| JP | 53-66192 | 3/1978 |
| JP | 5-76483 | 3/1993 |
| JP | 5-137693 | 6/1993 |
| JP | 6-43989 | 6/1994 |
| JP | 07-184837 | 7/1995 |
| JP | 7-184837 | 7/1995 |
| JP | 8-110479 | 4/1996 |
| JP | 10-165027 | 6/1998 |
| JP | 2001-224553 | 8/2001 |

OTHER PUBLICATIONS

Translated Office Action of Application No. 2001-537612 dated Apr. 18, 2008.

*Primary Examiner*—Vincent Boccio
(74) *Attorney, Agent, or Firm*—Pearl Cohen Zedek Latzer, LLP

(57) ABSTRACT

The present invention relates to a method for activating an image collecting process, comprising the step of releasing the power source of a component essential to the image collecting process from an inhibition imposed by an external magnet.

In an embodiment of the invention the image collecting process is designed to image the insides of a body lumen.

The present invention further relates to a packaging suitable for storing therein an imaging system, said package comprising a magnet. The imaging system comprises components essential to an image collecting process, said components operable in accordance with the invention.

10 Claims, 2 Drawing Sheets

METHOD FOR ACTIVATING AN IMAGE COLLECTING PROCESS

PRIOR APPLICATION DATA

The present application is a continuation of prior U.S. application Ser. No. 10/130,326, filed on May 15, 2002, now U.S. Pat. No. 7,295,226 and entitled "METHOD FOR ACTIVATING AN IMAGE COLLECTING PROCESS", which in turn is a national phase application of International Application Serial No. PCT/IL00/00752, entitled "METHOD FOR ACTIVATING AN IMAGE COLLECTING PROCESS", filed on Nov. 15, 2000, which in turn claims priority from Israel application 132944, filed on Nov. 15, 1999, all of which are hereby incorporated by reference herein in their entirety.

FIELD OF THE INVENTION

The present invention generally relates to a method for the activation of an image collecting process. More specifically, the method of the present invention can be applied to an image collecting process meant for imaging the inside of body lumens.

BACKGROUND OF THE INVENTION

Single chip imaging devices such as charge coupled devices (CCD) and CMOS type image sensors can operate using small power sources and relatively little energy. Such imaging devices are implemented in applications as diverse as star tracking applications and imaging the inside of the gastrointestinal tract.

For example, U.S. Pat. No. 5,604,531, assigned to the common assignee of the present invention, describes a swallowable capsule for imaging the full length of the gastrointestinal tract The swallowable capsule includes a camera system, an optical system for imaging an area of interest onto the camera system and a transmitter which transmits the video output of the camera system In some instances the imaging devices are inaccessible to an operator at the appropriate time for activation, such as for reasons of sterility, and must be activated by remote control such as by IR or radio.

A method for activating a battery, though not a battery of an imaging device, is exemplified in PED Inc's swallowable temperature pill. PED Inc. advertises a swallowable temperature pill for tracking core body temperature. The temperature pill is powered by a silver oxide battery. The battery is kept turned off during storage by a small magnet that is taped to the pill package and is activated by removing this magnet.

SUMMARY OF THE INVENTION

The present invention relates to a method for activating an image collecting process, comprising the step of releasing the power source of a component essential to the image collecting process from an inhibition imposed by an external magnet. The method enables facile and sterile activation of the image collecting process, since activation of the process does not require directly handling any component participating in the process and does not require a third party, such as a remote control operator An image collecting process is a process in which images are obtained and components essential to the image collecting process are those power source driven components whose operation is necessary for obtaining an image. Components essential to the image collecting process may be an imaging device, such as low energy imaging devices, i.e., a CCD camera or a CMOS type image sensor, a light source for illuminating the target to be imaged, etc.

The term power source of a component essential to the image collecting process includes a motor or an engine which utilize a power source for operating the component.

The term "external magnet" in the present invention refers to a magnet positioned relatively to the component or components essential to the image collecting process, such that it is capable of inhibiting the essential component or components power source.

In an embodiment of the invention the image collecting process is designed to image the insides of a body lumen. The essential components can be a part of or attached to a medical device that is inserted into the body lumen, such as a needle, stent, endoscope or a swallowable capsule The external magnet is part of or attached to the medical device package and is removed once the device package is removed.

The present invention further relates to a packaging suitable for storing therein an imaging system, said package comprising a magnet. The imaging system comprises components essential to an image collecting process, said components operable in accordance with the invention.

The present invention still further relates to a method for imaging a body lumen comprising the steps of:
 a) providing an imaging system inserted in a balancing cup, said imaging system comprising a camera system having video output; an optical system for imaging an area of interest onto said camera system; a transmitter which transmits the video output of said camera system;
 b) activating within the imaging system an image collecting process;
 c) releasing the imaging system from the balance cup; and
 d) inserting the imaging system into a body lumen The imaging system may also comprise other components such as a light source for illuminating an area of interest, a reception system which receives the transmitted video output, etc.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

The method of the present invention comprises the step of releasing the power source of any component essential to an image collecting process, of an inhibition imposed by an external magnet.

The essential components are those power source driven components whose operation is necessary for obtaining images. Essential components for obtaining images are, for example, an imaging device or an illumination source (depending on the requirements and sensitivity of the imaging device). The imaging device can be any image sensor suitable for use in the method of the present invention, such as CCD cameras or CMOS image sensors. The energy for the imaging device is usually supplied through a low energy motor comprising either an electrical or permanent magnet.

The external magnet can be either more powerful than the essential component motor magnet or aligned with the essential component motor magnet such as to neutralize its magnetic field. Thus, proximity of the external magnet to the essential component power source or motor acts to inhibit the activation of the image collecting process since components essential for the image collecting process are not operative.

The external magnet may be distanced from the essential component power source or motor, so as to enable the essential component operation, directly by an operator or by mechanical or other means, suitable for distancing the external magnet from the essential component power source or motor.

In one embodiment of the invention an imaging device is attached to or is a part of a medical device that is suitable for imaging the inside of body lumens, such as blood vessels, the gastrointestinal tract, etc. The medical device may be a stent, needle, endoscope or swallowable capsule, or any other device suitable for being inserted into body lumens.

Figure 1:
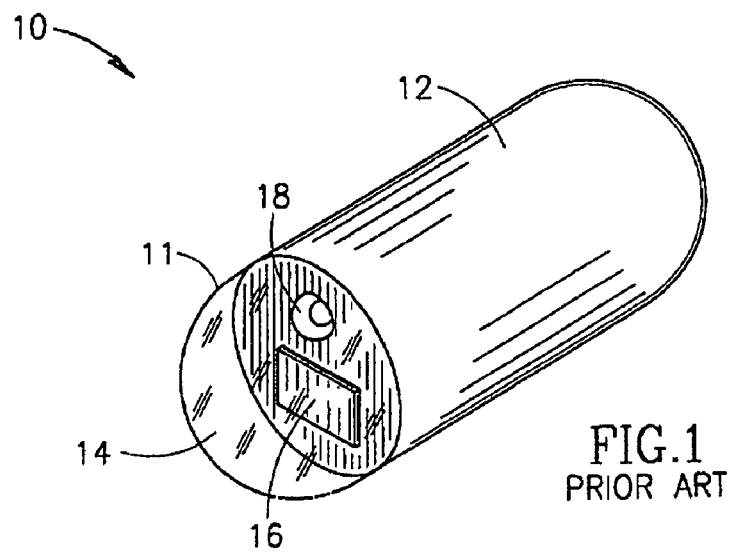
FIG. 1 is a schematic illustration of a prior art swallowable capsule comprising an imaging device.

Reference is now made to FIG. 1 which shows a schematic illustration of a prior art swallowable capsule comprising an imaging device. Such a swallowable capsule is described in U.S. Pat. No. 5,604,531. U.S. Pat. No. 5,604,531, which is assigned to the common assignees of the present invention, is hereby incorporated by reference.

Swallowable capsule 10 typically comprises a viewing unit 11 and a unit 12 housing the electrical elements of the capsule. The viewing unit 11 contains an imaging system which includes a light source 18, a viewing window 14 through which the light illuminates the inner portions of the digestive system, the image collector component of an imaging device 16, such as a charge coupled device (CCD) camera, which detects the images, an optical system (not shown) which focuses the images onto the image collector component of the imaging device 16, and means for transmitting the video signal of the imaging device. The imaging system may also include a reception system which is in communication with the imaging device and which receives the transmitted video output.

The unit 12 typically includes the electronics and power source for producing a video signal from the output of the CCD device and a power source, such as a battery, which provides power to the entirety of electrical elements of the capsule.

Figure 2:
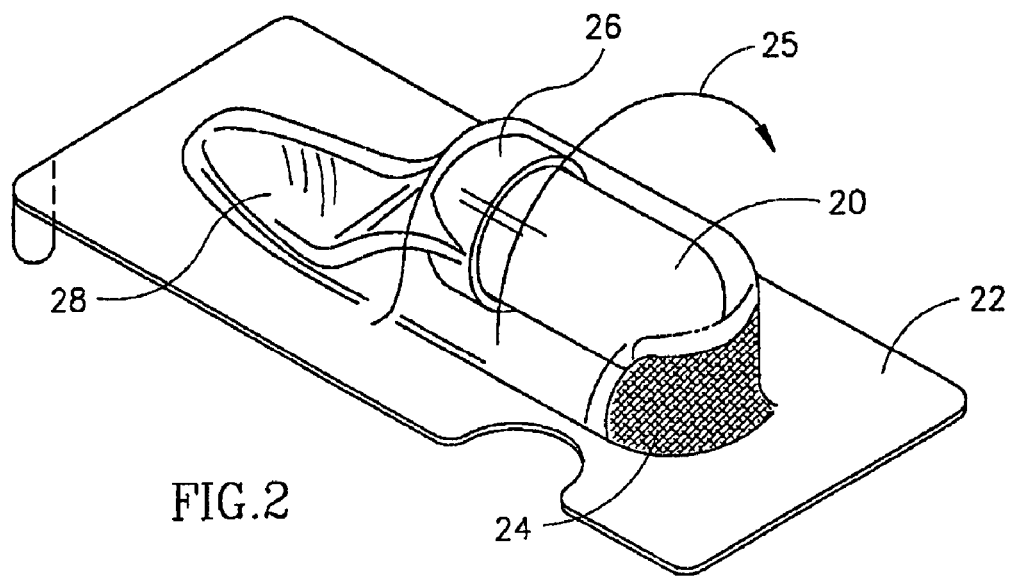
FIG. 2 is a schematic illustration of an imaging device in a package in accordance with an embodiment of the invention.
Figure 3:
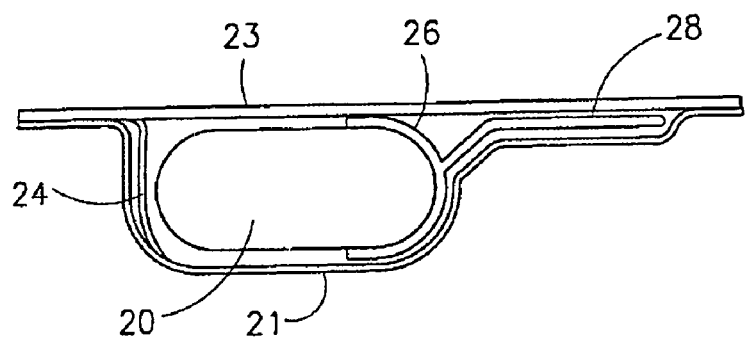
FIG. 3 is a side view of the imaging device and package illustrated in FIG. 2

Reference is now made to FIGS. 2 and 3 which are schematic overview and side views of a swallowable capsule 20 in a package 22 in accordance with an embodiment of the invention. Capsule 20 is similar to the capsule described in FIG. 1. The viewing unit of the capsule 20 is inserted in a white balance cup 26, which in turn is attached to a holder 28, for sterile handling of the capsule 20. Capsule 20, holder 28 and balance cup 26 are encased in package 22 which comprises a magnet 24. The package 22 also includes a base 23 (FIG. 3) and a transparent sterile upper plastic cover 21 (FIG. 3). The magnet 24 is positioned in alignment with the encased capsule 20 such that the magnet 24 inhibits the imaging device power source or inhibits the battery which provides power to the entirety of electrical elements of the capsule.

The magnet 24 may be ring shaped or curved (as illustrated in FIG. 2) so that no specific directionality of the capsule, in relation to the magnet, is required.

The imaging system in capsule 20, while the capsule 20 is still in the package 22, is inactive due to the proximity of the magnet 24. The imaging device and/or other power source driven components of the capsule 20 are activated once the capsule is distanced from the magnet 24, namely by removing the capsule 20 from the package 22. The capsule 20 may be removed from the package 22 by peeling off either base 23 or cover 21 in the direction shown by arrow 25 and extracting the holder 28, balance cup 26 and capsule 20 inserted therein.

The package 22 may be made of any material suitable for storing capsule 20. For example, package 22 may be a blister type package in which cover 21 is made of a firm but flexible plastic and base 23 is a foil of material which can be ruptured by pressure applied by a user. Capsule 20 is released from the package 22 by exerting pressure on it, through the cover 21 in the direction of the base 23 of the package 22, until the base 23 is ruptured, releasing the holder 28, balance cup 26 and capsule 20 inserted therein.

Once the capsule 20 is released from package 22 it is distanced from magnet 24 and the imaging device and/or other components essential for the imaging collecting process in capsule 20 are activated and the imaging system begins capturing images. Having the viewing unit of the capsule 20 inserted in a white balance cup 26, ensures that the first images captured and transmitted are white, thus enabling automatic white balance. The capsule 20 can be snapped out of the balance cup 26 to be swallowed by the patient.

In another embodiment the balance cup is marked on its inner wall, which is the wall being imaged once the image collecting process initiates. The image collecting process is operated for a predetermined initial period, prior to being released from the balance cup, during which identification of the mark is preformed. The image collecting process will be allowed to proceed only if identification of the mark is positive.

The mark may be a company logo or any other emblem or string of characters. The mark may be used, inter alia, to ensure that all parts of the imaging system are compatible, for example, that the capsule and its imaging device are compatible with the reception system and its software.

Figure 4:
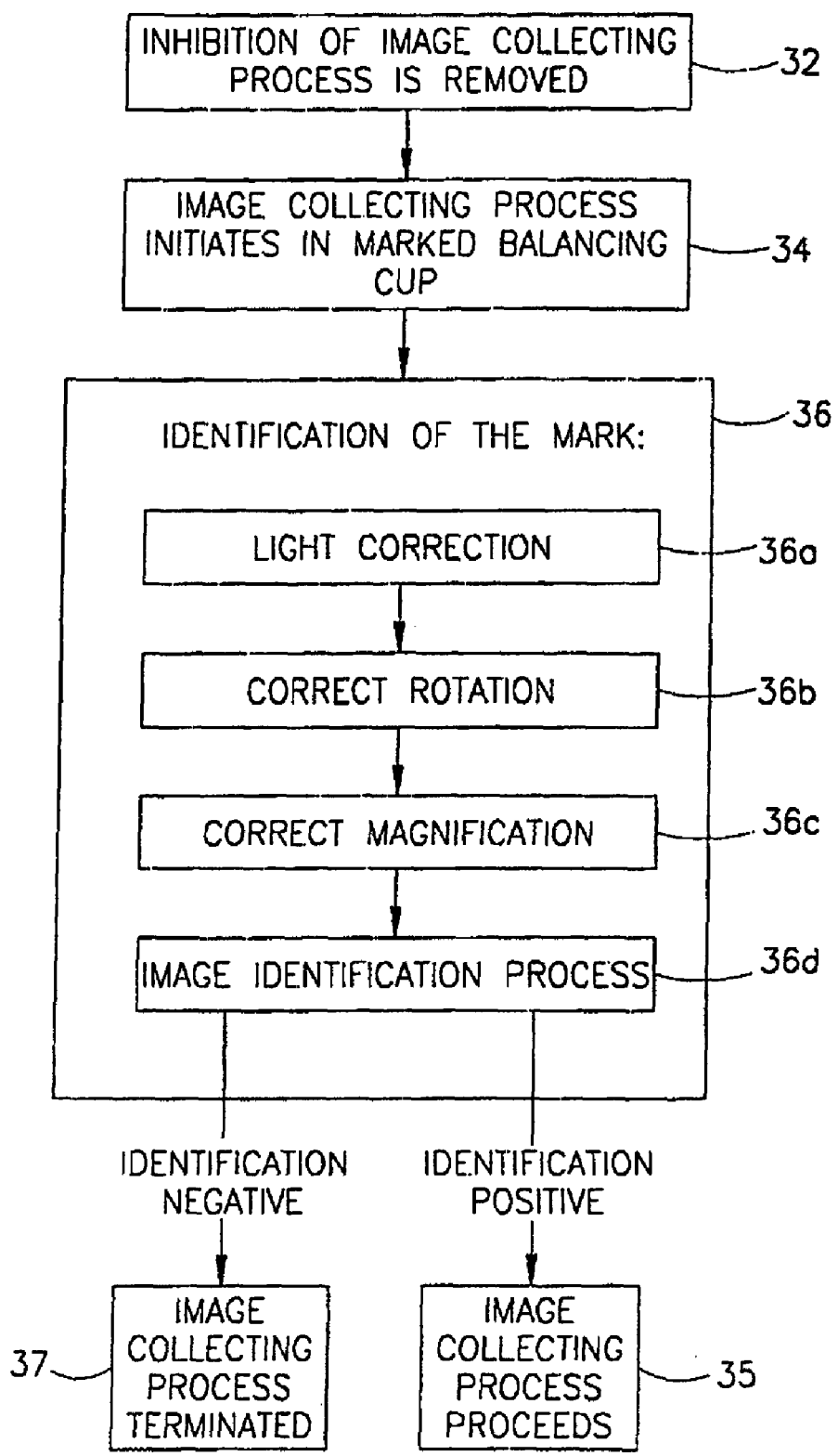
FIG. 4 is a block diagram of the method of the invention according to an embodiment of the invention.

This point is demonstrated by the block diagram presented in FIG. 4.

Inhibition of the power source of any component essential to the image collecting process is removed (32) and the image collecting process initiates (34). As discussed above, the first images collected will be images of the balance cup inner walls and of any mark on the balance cup inner wall. This initial data received from the imaging device is perceived by a reception system which is in communication with the imaging device and a process of identification of the mark (36) is initiated. The following factors, for example, might require adjustment for accurate identification of the mark:

a) The light conditions might vary between different capsules due to environment light and due to differences in the electronic components of the capsule (such as the light source and sensor);
b) The capsule and balance cup are not necessarily aligned, which will cause the image of the mark to appear in a different rotation angle each time;
c) The distance from the actual image is not accurate which results in different sizes of the object in the image; and
d) The image of the mark needs to be compared to a reference image and similarity needs to be confirmed.

Various algorithms may be executed to ensure accurate identification of the mark. For example, the following algorithms are executed in order to overcome the above:

Light correction (36a) is performed using an algorithm similar to AGC (Automatic Gain Control). This algorithm measures some statistical parameters of the input image. (The image is divided into 8×8 blocks and the average intensity is calculated. From this array average intensity and minimum and maximum block intensity are calculated.) Next, the brightness and contrast of the image are changed in order to bring the statistical parameters to a reference value.

In order to correct rotation (36b) the image is converted from Cartesic coordination into polaric coordination (from X,Y plane into R, Theta plane), where R=SQRT(X*X+Y*Y) and Theta=ATAN(X/Y).

After the conversion of the image into R, Theta plane, the magnification is corrected (36c) by applying a LOG function to the image. This function converts magnification, which is actually multiplication by a factor, into a bias/shift difference.

The identification of the mark is done by an image identification process (36d) in which the cross correlation function between a reference image and the input image is calculated and the maximum value of this cross correlation function is calculated. This maximum value is compared to a threshold. If it is higher than the threshold then the conclusion is that the images are similar.

If the result is that the images are similar (identification is positive), the image collecting process is allowed to proceed (35). If the result is that the images are not similar (identification is negative), the image collecting process is terminated (37).

Thus, the system will operate initially, for a predetermined time or to collect a predetermined number of frames, but the image collecting process will be allowed to continue further than the initial operation only if identification of the mark is positive. This mode of operation can be utilized to ensure that the system will only operate when all its components are the original components. For example, an original reception system that is used with a swallowable capsule from a different make (that does not have a marked balance cup) will not operate after the initial operation, because there will not be a positive identification of the mark.

The patient may be alerted if the image collecting process has terminated before swallowing the capsule.

The fact that the system is inoperable when unauthorized components are being used and the fact that the patient is warned greatly contributes to the patients safety.

It will be appreciated that algorithms and calculations are carried out by software or software means executable on computing means such as a computer or similar data processors, microprocessors, embedded processors, microcomputers, micrcontrollers etc.

The capsule may be utilized for diagnostic purposes or can be implemented in therapeutic processes. The capsule can also include any known system for collecting or releasing substances from or into the gastrointestinal tract environment, such that samples may be collected or medicaments may be released from the capsule at required points along the gastrointestinal tract. It will be appreciated that the image collecting process enables precise identification of required points and accurate localization of the capsule along the tract.

The method and packaging of the present invention enable safe activation of an image collecting process directly prior to use thereby providing safe, economic and facile use of components in an image collecting process.

It will be appreciated by persons skilled in the art that the present invention is not limited by what has been particularly shown and described herein above. Rather the scope of the invention is defined by the claims which follow:

The invention claimed is:

1. A method for operating a swallowable imaging capsule, the method comprising:
    magnetically activating a swallowable imaging capsule while the swallowable imaging capsule is in a cup to illuminate at least once from outside a patient's body, wherein the swallowable imaging capsule is within the cup such that a portion of the swallowable imaging capsule is held by the cup and a portion of the swallowable imaging capsule protrudes from the cup such that the swallowable imaging capsule can be released from the cup by a user;
    illuminating an area of interest inside the patient's body;
    transmitting an image of the area of interest to the reception system; and
    receiving at a reception system outside the patient's body output transmitted from the swallowable imaging capsule.

2. The method of claim 1, wherein the cup is to provide white balance.

3. The method according to claim 1 wherein the capsule comprises an imaging device, wherein the imaging device is a CCD camera or a CMOS type image sensor.

4. A method according to claim 1 wherein the capsule is designed to image the insides of body lumens.

5. A system for imaging the gastrointestinal tract, the system comprising:
    a swallowable capsule, said capsule comprising an imaging device; and
    a holding cup, wherein the capsule is removably inserted in the holding cup, and wherein capturing an image by the imaging device is started within the holding cup, allowing the verification of the system's operation based on images captured within the holding cup.

6. The system according to claim 5 wherein the imaging device comprises a CCD.

7. The system according to claim 5 wherein the imaging device comprises a CMOS.

8. The system according to claim 5 wherein the swallowable capsule comprises a light source.

9. The system according to claim 5 wherein the swallowable capsule comprises a transmitter for transmitting output of the imaging device.

10. The system according to claim 5 further comprising a reception system for receiving transmitted video output.

* * * * *